United States Patent
Baker et al.

(10) Patent No.: US 11,045,441 B2
(45) Date of Patent: Jun. 29, 2021

(54) USE OF RETINOIC ACID AND ANALOGS THEREOF TO TREAT CENTRAL NEURAL APNEAS

(71) Applicant: Wisconsin Alumni Research Foundation, Madison, WI (US)

(72) Inventors: Tracy Lee Baker, Verona, WI (US); Gordon Mitchell, Gainesville, FL (US); Daryl Fields, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/292,699

(22) Filed: Oct. 13, 2016

(65) Prior Publication Data

US 2017/0100358 A1 Apr. 13, 2017

Related U.S. Application Data

(60) Provisional application No. 62/240,684, filed on Oct. 13, 2015.

(51) Int. Cl.
*A61K 31/203* (2006.01)
(52) U.S. Cl.
CPC .................. *A61K 31/203* (2013.01)
(58) Field of Classification Search
CPC .................................................. A61K 31/203
USPC ........................................................ 514/559
See application file for complete search history.

(56) References Cited

U.S. PATENT DOCUMENTS

| | | |
|---|---|---|
| 4,193,931 A | 3/1980 | Loegliger |
| 4,539,134 A | 9/1985 | Martin et al. |
| 4,801,733 A | 1/1989 | Wuest et al. |
| 4,831,052 A | 5/1989 | Shudo |
| 4,833,240 A | 5/1989 | Maignan et al. |
| 4,874,747 A | 10/1989 | Shroot et al. |
| 4,879,284 A | 11/1989 | Lang et al. |
| 4,889,847 A | 12/1989 | Kligman et al. |
| 4,898,864 A | 2/1990 | Maignan et al. |
| 4,925,979 A | 5/1990 | Shudo |
| RE33,533 E | 2/1991 | Shroot et al. |
| 5,004,730 A | 4/1991 | Phillippe et al. |
| 5,124,473 A | 6/1992 | Shroot et al. |
| 5,198,567 A | 3/1993 | Lang et al. |

(Continued)

FOREIGN PATENT DOCUMENTS

| | | |
|---|---|---|
| EP | 0253393 A2 | 1/1988 |
| EP | 0266992 A2 | 5/1988 |

(Continued)

OTHER PUBLICATIONS

Day et al. (Respirology. Nov. 2009; 14(8):1134-1142).*

(Continued)

*Primary Examiner* — Sabiha N Qazi
(74) *Attorney, Agent, or Firm* — Joseph T. Leone, Esq.; DeWitt LLP

(57) ABSTRACT

Described is a method of inhibiting central apnea, central hypopnea or obstructive sleep apnea in a mammal. The method includes the step of administering to a mammal a central apnea inhibitory-effective, central hypopnea inhibitory-effective or obstructive sleep apnea inhibitory-effective amount of a composition comprising at least one retinoid or retinoid or retinoic acid receptor agonist.

5 Claims, 5 Drawing Sheets

(56) References Cited

U.S. PATENT DOCUMENTS

| | | | |
|---|---|---|---|
| 5,391,569 | A | 2/1995 | Brion et al. |
| 5,399,586 | A | 3/1995 | Davies et al. |
| 5,693,493 | A | 12/1997 | Robinson et al. |
| 5,801,253 | A | 9/1998 | Klaus et al. |
| 5,968,493 | A | 10/1999 | Dornoff |
| 6,030,964 | A | 2/2000 | Hibi et al. |
| 6,133,309 | A | 10/2000 | Boltag et al. |
| 6,147,244 | A | 11/2000 | McKenna et al. |
| 6,593,493 | B1 | 7/2003 | Ardecky et al. |
| 7,166,570 | B2 * | 1/2007 | Hunter .................. A61B 17/11 514/21.92 |
| 7,432,301 | B2 * | 10/2008 | Gaston .................. A61K 31/00 514/1.1 |
| 7,655,699 | B1 | 2/2010 | Boehm et al. |
| 8,343,996 | B2 * | 1/2013 | Duggan ............. A61K 31/4375 514/300 |
| 2005/0147643 | A1 * | 7/2005 | Hunter .................. A61B 17/11 424/423 |
| 2013/0189319 | A1 * | 7/2013 | Cook .................. A61K 31/216 424/400 |

FOREIGN PATENT DOCUMENTS

| | | | |
|---|---|---|---|
| EP | 0718285 | A2 | 6/1996 |
| WO | WO 93/21146 | A1 | 10/1993 |
| WO | WO 94/12880 | A2 | 6/1994 |
| WO | WO 94/15901 | A1 | 7/1994 |
| WO | WO 94/15902 | A1 | 7/1994 |
| WO | WO 94/17796 | A1 | 8/1994 |
| WO | WO 94/20093 | A1 | 9/1994 |
| WO | WO 95/04036 | A1 | 2/1995 |
| WO | WO 96/05165 | A1 | 2/1996 |

OTHER PUBLICATIONS

Nathan A. Baertsch et al.(J Neurophysiol 118:2702-2710, 2017. First published Aug. 16, 2017; doi:10.1152/jn.00212.2017, Intermittent apnea elicits inactivity-induced phrenic motor facilitation via a retinoic acid- and protein synthesis-dependent pathway).*

Abraham, D. and Rotella, D., "Burger's Medicinal Chemistry and Drug Discovery, 7$^{th}$ Ed." © 2010 John Wiley & Sons, Inc. Hoboken, NJ, ISBN 978-0470278154 (Book—Copy Not Provided).

Allegretto, E. et al (1995) "Retinoid X Receptor Acts as a Hormone Receptor in Vivo to Induce a Key Metabolic Enzyme for 1,25-Dihydroxyvitamin D$_3$," J. Biol.Chem., 270:23906-23909.

Beard, R.L. et al (1995) "Synthesis and Structure-Activity Relationships of Stilbene Retinoid Analogs Substituted with Heteroaromatic Carboxylic Acids," J. Med. Chem., 38(15):2820-2829.

Boehm, H. et al (1994) "Synthesis and Structure-Activity Relationships of Novel Retinoid X Receptor-Selective Retinoids," J. Med. Chem., 37(18):2930-2941.

Boehm, M. et al (1995) "Design and Synthesis of Potent Retinoid X Receptor Selective Ligands That Induce Apoptosis in Leukemia Cells," J. Med. Chem., 38(16):3146-3155.

Bundgard, H., "Design of Prodrugs," © 1985 Elsevier Science Ltd., Amsterdam, ISBN 978-0444806758 (Book—Copy Not Provided).

Dawson, M.I. et al (1989) "Effect of structural modifications in the C7-C11 region of the retinoid skeleton on biological activity in a series of aromatic retinoids," J. Med. Chem., 32(7):1504-1517.

"Handbook of Pharmaceutical Salts, Properties, Selection, and Use," P.H. Stahl and C.G. Wermuch, Eds., © 2008, Wiley-VCH (Zurich, Switzerland), ISBN: 978-3-90639-058-1 (Book—Copy Not Provided).

Kagechika, H. et al. (1989)—6 "Retinobenzoic acids. 2. Structure-activity relationships of chalcone-4-carboxylic acids and flavone-4'-carboxylic acids," J. Med. Chem., 32(4): 834-840.

Kagechika, H. et al. (1989)—7 "Retinobenzoic acids. 3. Structure-activity relationships of retinoidal azobenzene-4-carboxylic acids and stilbene-4-carboxylic acids," J. Med. Chem., 32(5):1098-1108.

Kagechika, H. et al. (1989)—8 "Retinobenzoic acids. 4. Conformation of aromatic amides with retinoidal activity. Importance of trans-amide structure for the activity," J. Med. Chem., 32(10):2292-2296.

Redasani, V. and Bari, S. "Prodrug Design: Perspectives, Approaches and Applications in Medicinal Chemistry," © 2015 Academic Press (an imprint of Elsevier), Waltham, MA, ISBN 978-0128035191 (Book—Copy Not Provided).

Sica et al., (2000) Chronic-intermittent hypoxia: a model of sympathetic activation in the rat, Respiration Physiology, 121: 173-184.

Simoni, D. et al, (2001) "Retinoic Acid and analogs as potent inducers of differentiation and apoptosis. New promising chemopreventive and chemotherapeutic agents in oncology," Pure Appl. Chem. 73(9):1437-1444.

Solomin, L. et al. (1998) "Retinoid-X receptor signaling in the developing spinal cord," Nature 395:398-402.

Sporn and Roberts, Retinoids: Biology, Chemistry and Medicine, © 1994 Lippincott Williams & Wilkins, Philadelphia, PA, ISBN 978-0781700825 (Book—Copy Not Provided).

* cited by examiner

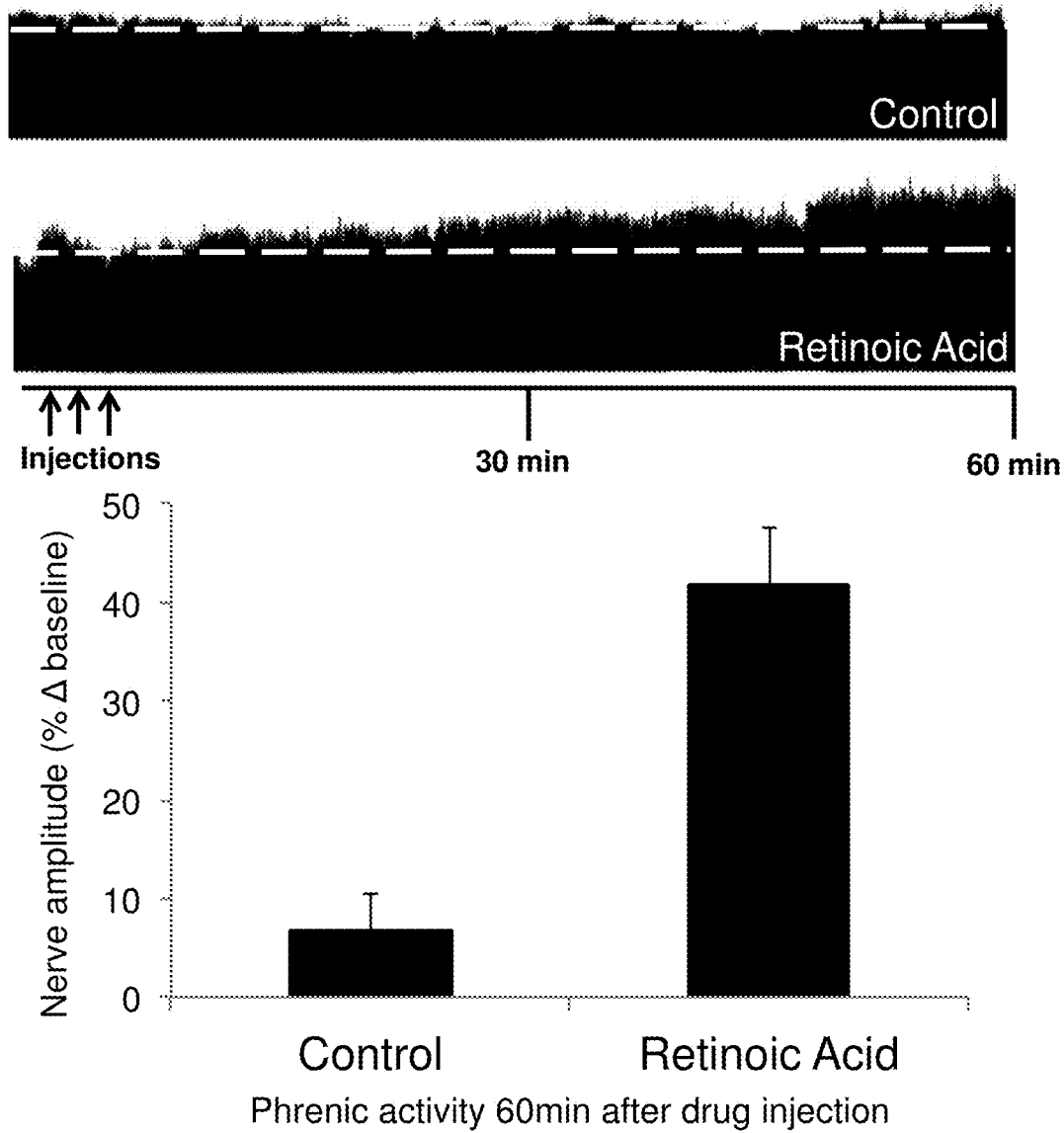

USE OF RETINOIC ACID AND ANALOGS THEREOF TO TREAT CENTRAL NEURAL APNEAS

CROSS-REFERENCE TO RELATED APPLICATIONS

Priority is hereby claimed to provisional application Ser. No. 62/240,684, filed Oct. 13, 2015, which is incorporated herein by reference.

FEDERAL FUNDING STATEMENT

This invention was made with government support under HL105511 and HL080209 awarded by the National Institutes of Health. The government has certain rights in the invention.

BACKGROUND

Central neural apnea, or simply neural apnea, is associated with multiple clinical disorders and reflects an impaired ability for subject's nervous system to maintain rhythmic breathing. The related condition respiratory neural hypopnea, or simply hypopnea, is a disorder in which a subject's breathing is abnormally shallow or the subject's respiratory rate is abnormally low (i.e., hypoventilation). Respiratory neural apneas and hypopneas originate in neural functions within the central nervous system, and differ from obstructive apneas in which breathing during sleep is limited because of an upper airway obstruction or defect. Central apnea/hypopnea is thus a type of disordered breathing characterized by failure of the respiratory control system to generate the regular, rhythmic bursts of respiratory nerve activity that trigger respiratory muscle contractions and breathing. The resulting pause in rhythmic breathing, the apnea, or a brief period of slow or shallow breathing (hypopnea), are symptoms of unstable respiratory control system function. Although central apnea/hypopnea occurs in multiple clinical settings, it is often observed during heart failure, chronic respiratory disease, neurodegenerative diseases, premature birth and/or cerebral vascular insufficiency.

The etiology of central sleep apnea/hypopnea is poorly understood. In broad terms, the mammalian respiratory control system includes negative feedback loops in which hypoxia- and carbon dioxide-sensitive chemoreceptors provide sensory feedback to the brain stem central pattern generator that creates rhythmic bursts of neural activity that are transformed into a breath. When chemoreceptors are activated or inhibited, breathing depth (i.e., normal tidal volume) and rate increase or decrease, respectively. If feedback from the carbon dioxide-sensitive chemo receptors is strongly suppressed, activity in the brain stem respiratory pattern generator is greatly reduced or goes completely silent, generating hypopnea or apnea, respectively. Typically, this would happen during sleep, when the so-called "wakefulness" drive to breathe is lost, hypoxic drive to breath is suppressed, and the resting level of carbon dioxide in the arterial blood is close the apneic threshold (see below).

During sleep, the amplitude of respiratory nerve activity depends on the partial pressure of carbon dioxide in the brain tissue and arterial blood. When the level of arterial carbon dioxide increases, the chemoreceptors stimulate the central pattern generator and increase tidal volume and breathing frequency. However, if arterial carbon dioxide levels decrease sufficiently during sleep, $CO_2$ chemoreceptor activity may decrease sufficiently to halt all breathing efforts, a level of arterial carbon dioxide partial pressure known as the $CO_2$ apneic threshold.

The intensity of respiratory neural activity is also inversely proportional to the arterial oxygen partial pressure. When arterial $O_2$ levels become quite low, a subset of chemoreceptors known as the peripheral or carotid body chemoreceptors is activated, increasing central pattern generator activity, respiratory nerve activity and breathing. As oxygen levels rise, the stimulatory input from $O_2$ chemoreceptors decreases, removing the influence of arterial oxygen on respiratory drive. Thus, the entire system can be viewed as being under the control of interlocking and dynamical feedback loops that strive to maintain reasonably normal arterial oxygen and carbon dioxide levels.

A critical determinant of ventilatory stability is the difference between the prevailing arterial $PCO_2$ during spontaneous breathing versus the arterial $PCO_2$ at the apneic threshold, a difference known as the $CO_2$ reserve. If spontaneous breathing during sleep results in an arterial $PCO_2$ that is too close to the $CO_2$ apneic threshold, periodic breathing and/or CSA may result, characterized by repeated cycles of low tidal volume (or complete cessation of breathing) followed by high tidal volume breaths. Periodic breathing or central sleep apnea reflects an abnormality or breakdown of the respiratory control system. For individuals suffering from central sleep apnea/hypopnea, hypoxemia develops during each apnea or hypopnea. Hypoxemia may promote cardiac arrhythmias, strokes or myocardial infarctions. In addition, prolonged, intermittent hypoxia during sleep causes serve morbidity, including systemic hypertension, pulmonary hypertension, metabolic syndrome, insomnia, daytime hypersomnolence, neuroinflammation and impaired cognitive function; collectively, this pathology diminishes the quality of life and shortens its duration. Currently, there is no standard treatment deemed effective to inhibit or otherwise ameliorate central sleep apnea/hypopnea in adults.

While central sleep apnea results when there is no neural activity in the nerves innervating the primary (diaphragm) or accessory (i.e., intercostals) muscles that generate a breath, obstructive sleep apnea is quite different, and results from impaired control of the nerves/muscles that maintain upper airway patency (e.g., the hypoglossal nerve that controls tongue contractions). Obstructive sleep apnea (OSA) occurs when there is inadequate drive to upper airway muscles leading to airway collapse and continued inspiratory breathing efforts against a closed airway. Thus, in OSA, subjects fail to generate respiratory airflow despite their attempts to breathe because of the upper airway occlusion, often due to a lack of motor input to the tongue from the hypoglossal nerve. Current OSA therapies attempt to relieve or minimize upper airway occlusions by surgically removing muscles that block the airway during sleep, or by creating a positive pressure in the upper airways that "splints" the airway open despite inadequate upper airway muscle tone (e.g., CPAP or continuous positive airway pressure). While surgery and CPAP masks provide relief for some patients, they do not address the loss of respiratory drive to upper airway muscles that underlies OSA. Further, because CPAP masks are cumbersome and inconvenient, they are often ineffective because of poor patient compliance.

Recently, the present inventors have identified a novel form of compensatory plasticity known as inactivity-induced respiratory motor facilitation that is induced by central neural apnea. Inactivity-induced respiratory motor facilitation is a prolonged enhancement in respiratory neural activity within hypoglossal nerve (innervating the tongue), the phrenic nerve (innervating the diaphragm), and the intercostal nerve (innervating the inspiratory intercostals), which results in increased breathing efforts (phrenic and intercostal nerves) and protected patency of the airway (hypoglossal nerve). In addition, inactivity-induced respiratory motor facilitation results in a lowering of the $CO_2$ apneic threshold. Through these actions, inactivity induced respiratory motor facilitation is thought to prevent future central and obstructive apneas by increasing motor input to the phrenic and hypoglossal nerves respectively. Retinoic acid synthesis is required for inactivity-induced respiratory motor facilitation, which is prevented by concurrent exposure to moderate hypoxia. Thus, concurrent moderate hypoxia, such as may be experienced in patients with moderate to severe sleep apnea, is thought to undermine induction of retinoic acid dependent respiratory motor facilitation, making subjects susceptible to central and obstructive sleep apneas.

Retinoic acid (hereinafter "RA") has several different isomers and analogs. For example, all-trans retinoic acid (hereinafter "ATRA") has been formulated into a wide variety of pharmaceutical compositions by several manufacturers. In the United States, pharmaceutical compositions containing ATRA are generically designated "tretinoin." ATRA has the following structure:

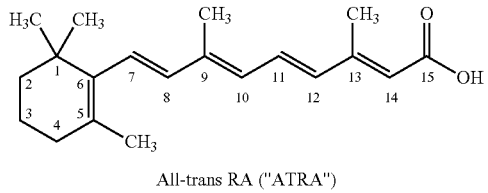

All-trans RA ("ATRA")

The 13-cis version of retinoic acid is commonly referred to as "isotretinoin," and has the following structure:

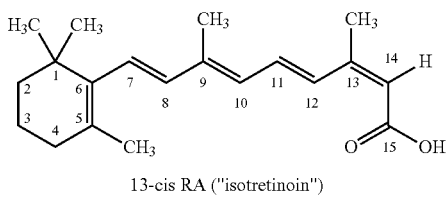 [SMILES: CC1=C(/C=C/C(C)=C/C=C/C(C)=C\C(=O)O)C(C)(C)CCC1]

13-cis RA ("isotretinoin")

Isotretinoin is marketed in the United States under the trademark "ACCUTANE" (Hoffmann-La Roche, Inc., Nutley, N.J.).

The 9-cis version of retinoic acid is commonly referred to as "alitretinoin," and has the following structure:

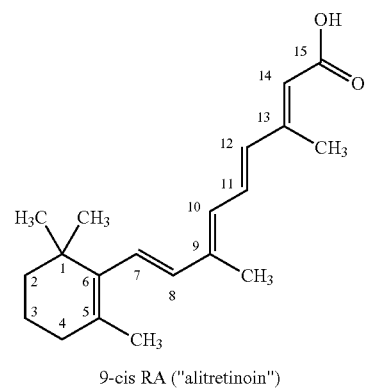 [SMILES: CC1=C(/C=C/C(C)=C/C=C/C(C)=C/C(=O)O)C(C)(C)CCC1]

9-cis RA ("alitretinoin")

SUMMARY OF THE INVENTION

Disclosed herein is a method of preventing, inhibiting, treating, managing and/or otherwise ameliorating central neural apnea, central neural hypopnea or obstructive sleep apnea in a mammal. The method comprising administering to a mammal a central neural apnea inhibitory-effective, central neural hypopnea inhibitory-effective or obstructive sleep apnea inhibitory-effective amount of a composition comprising at least one retinoid. Preferred retinoids for use in the method include, but is not limited to, ATRA, 13-cis RA or 9-cis RA. The method includes administering to a mammalian subject a therapeutically effective amount of at least one retinoid as described herein, or a pharmaceutically acceptable form thereof (e.g., salts, hydrates, solvates, isomers, prodrugs, and isotopically labeled derivatives).

Where the method is directed to preventing central neural apnea, central neural hypopnea or obstructive sleep apnea in a mammal, the method comprises administering to a mammalian subject a prophylactically effective amount (i.e., a central neural apnea preventative-effective, central neural hypopnea, or obstructive sleep apnea preventative-effective amount) of at least one retinoid as described herein or a pharmaceutically acceptable form thereof (e.g., salts, hydrates, solvates, isomers, prodrugs, and isotopically labeled derivatives).

Also provided are pharmaceutical compositions (e.g., single unit dosage forms) that can be used in the methods disclosed herein. The pharmaceutical compositions are effective to prevent, inhibit, treat, manage and/or otherwise ameliorate central neural apnea or central neural hypopnea in a mammal, including humans.

BRIEF DESCRIPTION OF THE DRAWINGS

FIG. 1A is a paired neurogram of phrenic nerve activity from baseline to 60 min following all trans-retinoic acid injections into the cervical spinal intrathecal space in rats vs untreated control rats. (See examples for complete details.)

FIG. 1B is a graph depicting phrenic nerve activity as a percentage of baseline activity in control rats versus rats injected with retinoic acid; measurements taken 60 min after final injection.

DETAILED DESCRIPTION

Abbreviations and Definitions

Figure 2A:
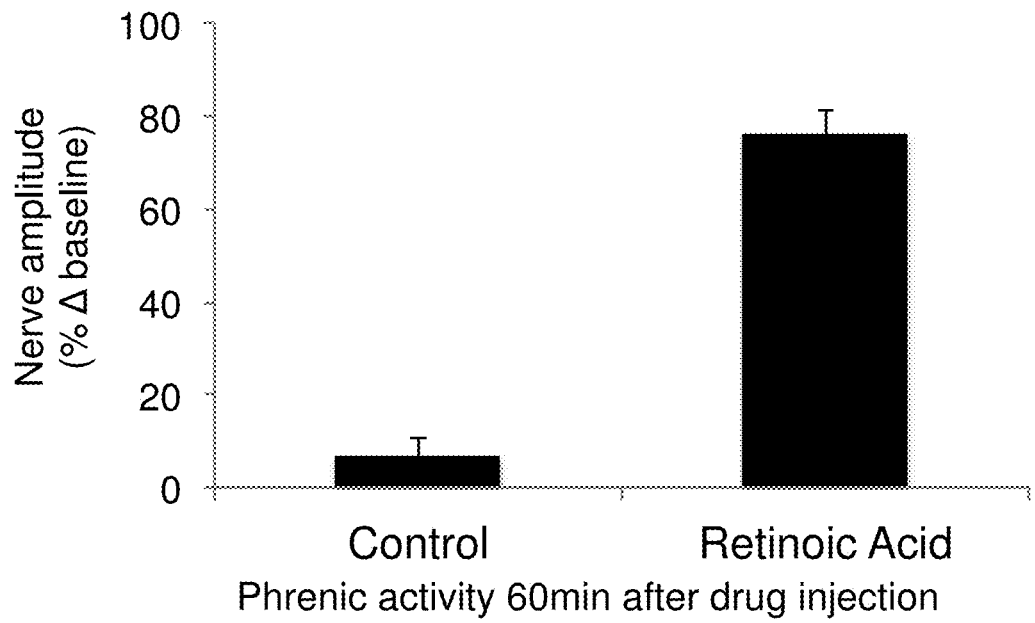
FIG. 2A is a graph depicting phrenic nerve activity as a percentage of baseline activity in control rats versus rats injected with retinoic acid; measurements taken 60 min after final injection.

ATRA=all-trans retinoic acid. CIH=chronic intermittent hypoxia. RA=retinoic acid. RAR=nuclear retinoic acid receptor. RXR=retinoic X receptor.

"Enteral" administration is administration of a pharmaceutically active ingredient that involves any part of the gastrointestinal tract and which results in systemic administration. Enteral administration thus includes oral administration, such as by tablets, capsules, or drops; administration by gastric feeding tube, duodenal feeding tube, or gastrostomy; and rectally via suppository or enema.

"Parenteral" administration is administration of a pharmaceutically active ingredient by any route other than via any part of the gastrointestinal tract. Thus, parenteral administration includes intravenous, intra-arterial, intramuscular, intraosseous, intracerebral, intracerebroventricular, intrathecal, and subcutaneous administration.

As used herein, "pharmaceutically acceptable esters" include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids.

As used herein, "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" or a "pharmaceutically suitable form" of a disclosed compound includes, but is not limited to, pharmaceutically acceptable salts, hydrates, solvates, isomers, prodrugs, and isotopically labeled derivatives of disclosed compounds.

A "pharmaceutically acceptable salt" or "pharmaceutically suitable salt" is any acid or base addition salt whose counter-ions are non toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. See, for example, "Handbook of Pharmaceutical Salts, Properties, Selection, and Use," P. H. Stahl and C. G. Wermuch, Eds., © 2008, Wiley-VCH (Zurich, Switzerland), ISBN: 978-3-90639-058-1.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. It will be understood that the term "compound" as used herein encompasses the compound and solvates of the compound, as well as mixtures thereof.

In certain embodiments, the pharmaceutically acceptable form of the retinoid is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism. See, for example, Bundgard, H., "Design of Prodrugs," © 1985 Elsevier Science Ltd., Amsterdam, ISBN 978-0444806758, and Redasani, V. and Bari, S. "Prodrug Design: Perspectives, Approaches and Applications in Medicinal Chemistry," © 2015 Academic Press (an imprint of Elsevier), Waltham, Mass., ISBN 978-0128035191, both of which are incorporated in full by reference herein. Exemplary advantages of a prodrug can include, but are not limited to, its physical properties, such as enhanced water solubility for parenteral administration at physiological pH compared to the parent compound, and/or enhanced absorption from the digestive tract, and/or enhanced drug stability for long-term storage.

The term "prodrug" also includes any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —$NO_2$, —ONO, or —$ONO_2$ moieties. Prodrugs can typically be prepared using well-known methods, such as those described in Abraham, D. and Rotella, D., "Burger's Medicinal Chemistry and Drug Discovery, $7^{th}$ Ed." © 2010 John Wiley & Sons, Inc. Hoboken, N.J., ISBN 978-0470278154, and in the Bundgaard reference and the Redasani & Bari reference noted previously.

For example, if a disclosed compound or a pharmaceutically acceptable form of the compound contains a carboxylic acid functional group, a prodrug may comprise a pharmaceutically acceptable ester formed by the replacement of the hydrogen atom of the acid group with a group such as $C_1$-$C_8$-alkyl, $C_2$-$C_{12}$-alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$C_1$-$C_2$-alkylamino-$C_2$-$C_3$-alkyl (such as 3-dimethylaminoethyl, carbamoyl-$C_1$-$C_2$-alkyl, N,N-di-$C_1$-$C_2$-alkylcarbamoyl-$C_1$-$C_2$-alkyl and piperidino-, pyrrolidino- or morpholino-$C_2$-$C_3$-alkyl.

Similarly, if a disclosed compound or a pharmaceutically acceptable form of the compound contains an alcohol functional group, a prodrug can be formed by the replacement of the hydrogen atom of the alcohol group with a group such as $C_1$-$C_6$-alkanoyloxymethyl, 1-($C_1$-$C_6$-alkanoyloxy)ethyl, 1-methyl-1-($C_1$-$C_6$-alkanoyloxy)ethyl, $C_1$-$C_6$-alkoxycarbonyloxymethyl, N—$C_1$-$C_6$-alkoxycarbonylaminomethyl, succinoyl, $C_1$-$C_6$-alkanoyl, α-amino-$C_1$-$C_4$-alkanoyl, arylacyl and α-aminoacyl, or α-aminoacyl-α-aminoacyl, where each α-aminoacyl group is independently selected from the naturally occurring L-amino acids, —P(O)$(OH)_2$, —P(O) (O—$C_1$-$C_6$-alkyl), or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $C_1$-$C_{10}$-alkyl, $C_3$-$C_7$-cycloalkyl, benzyl, a natural α-aminoacyl or natural α-aminoacyl-natural α-aminoacyl, —C(OH)C(O)$OY^1$ wherein $Y^1$ is H, $C_1$-$C_6$-alkyl or benzyl, —C($OY^2$)$Y^3$ wherein $Y^2$ is C—$C_4$-alkyl and $Y^3$ is $C_1$-$C_6$-alkyl, carboxy-$C_1$-$C_6$-alkyl, amino-$C_1$-$C_4$-alkyl or mono-N— or di-N,N—$C_1$-$C_6$-alkylaminoalkyl, —C($Y^4$)$Y^5$ wherein $Y^4$ is H or methyl and $Y^5$ is mono-N— or di-N,N—$C_1$-$C_6$-alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (1)-isomers, single isomers thereof, mixtures thereof, racemic mixtures thereof, and enantiomerically enriched mixtures thereof.

Geometric isomers can be represented by dashed bonds, which denote bonds that can be a single, double or triple bonds. Provided herein are various geometric isomers and mixtures thereof resulting from the arrangement of substituents around a carbon-carbon double bond. Substituents around a carbon-carbon double bond are formally designated as being in the Z configuration (German "zusammen"—"together") or E configuration (German "entgegen"—"opposite"), but more typically identified as being either "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" designates substituents on the same side of the plane of the ring, and the term "trans" designates substituents on opposite sides of the plane of the ring.

As used herein, the term "retinoid" refers to any natural or synthetic compound that binds to the retinoic acid receptor ("RAR") and/or the retinoic X receptor ("RXR"). See, for example, Sporn and Roberts, Retinoids: Biology, Chemistry and Medicine," 01994 Lippincott Williams & Wilkins, Philadelphia, Pa., ISBN 978-0781700825, the content of which is incorporated herein by reference. The term "retinoid" explicitly includes, but is not limited to, ATRA, 13-cis RA, 9-cis RA, tazarotene, and the retinoids described in the following references: U.S. Pat. Nos. 4,666,941, 4,581,380, EP 0210929, EP 0232199, EP 0260162, EP 0292348, EP 0325540, EP 0359621, EP 0409728, EP 0409740, EP 0552282, EP 0584191, EP 0514264, EP 0514269, EP 0661260, EP 0661258, EP 0658553, EP 0679628, EP 0679631, EP 0679630, EP 0708100, EP 0709382, EP 0722928, EP 0728739, EP 0732328, EP 0749937, EP 0776885, EP 0776881, EP 0823903, EP 0832057, EP 0832081, EP 0816352, EP 0826657, EP 0874626, EP 0934295, EP 0915823, EP 0882033, EP 0850909, EP 0879814, EP 0952974, EP 0905118, EP 0947496, WO98/56783, WO99/10322, WO99/50239 and WO99/65872. Preferred retinoids include retinoic acid, all-trans retinoic acid, 13-cis-retinoic acid, 9-cis-retinoic acid, esters thereof, salts thereof, and metabolic precursors thereof.

A "retinoid" as the term is defined herein is also an agonist of one or both of RAR and/or RXR. Standard in vitro tests for receptor binding may be carried out to determine binding to RAR and RXR for any given retinoid. See, for example, Simoni, D. et al, (2001) "Retinoic Acid and analogs as potent inducers of differentiation and apoptosis. New promising chemopreventive and chemotherapeutic agents in oncology," Pure Appl. Chem. 73(9):1437-1444. RAR and RXR retinoid agonists, including both RAR-specific and RXR-specific agonists have been previously identified. In addition to the references noted earlier, see also WO 94/15902, WO 93/21146, WO 94/15901, WO 94/12880, WO 94/17796, WO 94/20093, WO 96/05165 and International Application No. PCT/US93/10166; European Patent Applications Nos. 87110303.2, 87309681.2 and EP 0718285; U.S. Pat. Nos. 4,193,931, 4,539,134, 4,801,733, 4,831,052, 4,833,240, 4,874,747, 4,879,284, 4,898,864, 4,925,979, 5,004,730, 5,124,473, 5,198,567, 5,391,569, Re 33,533, 5,693,493, 5,968,493, 6,030,964, 6,133,309, 6,147,244, and 6,593,493.

See also Kagechika, H. et al. (1989) "Retinobenzoic acids. 2. Structure-activity relationships of chalcone-4-carboxylic acids and flavone-4'-carboxylic acids," *J. Med. Chem.*, 32(4): 834-840; Kagechika, H. et al. (1989) "Retinobenzoic acids. 3. Structure-activity relationships of retinoidal azobenzene-4-carboxylic acids and stilbene-4-carboxylic acids," *J. Med. Chem.*, 32(5):1098-1108; Kagechika, H. et al. (1989) "Retinobenzoic acids. 4. Conformation of aromatic amides with retinoidal activity. Importance of trans-amide structure for the activity," *J. Med. Chem.*, 32(10):2292-2296; Boehm, H. et al (1994) "Synthesis and Structure-Activity Relationships of Novel Retinoid X Receptor-Selective Retinoids," *J. Med. Chem.*, 37(18): 2930-2941; Boehm, M. et al (1995) "Design and Synthesis of Potent Retinoid X Receptor Selective Ligands That Induce Apoptosis in Leukemia Cells," *J. Med. Chem.*, 38(16):3146-3155; Allegretto, E. et al (1995) "Retinoid X Receptor Acts as a Hormone Receptor in Vivo to Induce a Key Metabolic Enzyme for 1,25-Dihydroxyvitamin D3," *J. Biol. Chem.*, 270:23906-23909; Solomin, L. et al. (1998) "Retinoid-X receptor signaling in the developing spinal cord," *Nature* 395:398-402; Beard, R. L. et al (1995) "Synthesis and Structure-Activity Relationships of Stilbene Retinoid Analogs Substituted with Heteroaromatic Carboxylic Acids," *J. Med. Chem.*, 38(15):2820-2829; and Dawson, M. I. et al (1989) "Effect of structural modifications in the $C_7$-$C_{11}$ region of the retinoid skeleton on biological activity in a series of aromatic retinoids," *J. Med. Chem.*, 32(7): 1504-1517.

The RAR and RXR retinoid agonists referred to in the above-referenced patent applications, patents, and scientific articles may be used in the method described and claimed herein. Methods to make retinoids, dosage ranges, and suitable pharmaceutical compositions and formulations are described in the various patent applications/patents and scientific articles referred to above, all of which are incorporated herein by reference.

Preferred retinoids include retinoic acid, all-trans retinoic acid, 9-cis-retinoic acid, as well as other retinoids as shown in Formula I:

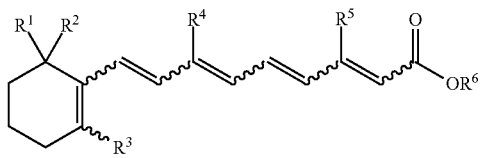

Formula I wherein $R^1$, $R^2$, $R^3$, $R^4$ and $R^5$ are the same or different and are independently selected from the group consisting of H, halogen, hydroxyl, $C_1$-$C_6$-alkyl, and $C_1$-$C_6$-alkoxy, and $R^6$ is selected from the group consisting of H and $C_1$-$C_6$-alkyl.

Methods and Pharmaceutical Compositions to Treat Central Sleep Apnea/Hypopnea:

Also disclosed herein are pharmaceutical compositions comprising one or more of the retinoids or pharmaceutically suitable forms thereof as described herein. More specifically, the pharmaceutical composition may comprise one or more of the retinoids as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, retinoids produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant retinoid(s).

For intravenous administration, the retinoid(s) may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative retinoid as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral, rectal, etc., as noted above) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the subject may be determined by one of ordinary skill in the art and depends upon various factors such as weight of the subject, age of the subject, immune status of the subject, etc., and is ultimately at the discretion of the medical or veterinary professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating central sleep apnea/hypopnea disorders in mammals, including humans, by administering an anti-central sleep apnea/hypopnea or obstructive sleep apnea effective amount of one or more the retinoids described herein. In particular, the compositions of the present invention may be used to treat central sleep apneas, hypopneas or obstructive sleep apnea of any and all description.

The above-described pharmaceutical compositions may be used with humans, as well as non-human mammals, both domesticated and feral.

EXAMPLES

The following examples are included solely to provide a more complete description of the method disclosed and claimed herein.

Methods:

Neurophysiology:

Respiratory-related activity was recorded from the left phrenic and hypoglossal nerves in urethane-anesthetized (1.7 g/kg), vagotomized, paralyzed and mechanically ventilated rats (see Strey et al., 2012 for details). Rats are slightly hyperventilated, so a small amount of inspired $CO_2$ was delivered to achieve target, normal $PCO_2$. A pre-study apneic threshold test was performed. The apneic threshold was determined by lowering arterial $PCO_2$ until phrenic respiratory activity ceased. To set baseline phrenic respiratory activity for the studies represented in the figures, arterial $PCO_2$ was slowly increased until phrenic activity resumed again; baseline phrenic activity was set 2-3 mm Hg above this $PCO_2$ level. Following 15 min of stable phrenic and hypoglossal burst discharge, baseline phrenic and hypoglossal burst amplitudes and blood gases were measured. Rats were then subjected to one of the following protocols:

Protocol 1) Three (3) 10 μL intrathecal injections (50 μM each) of retinoic acid or three (3) 10 μL of vehicle (aCSF in 10% DMSO). The results are depicted in FIGS. 1A and 1B.

Figure 2B:
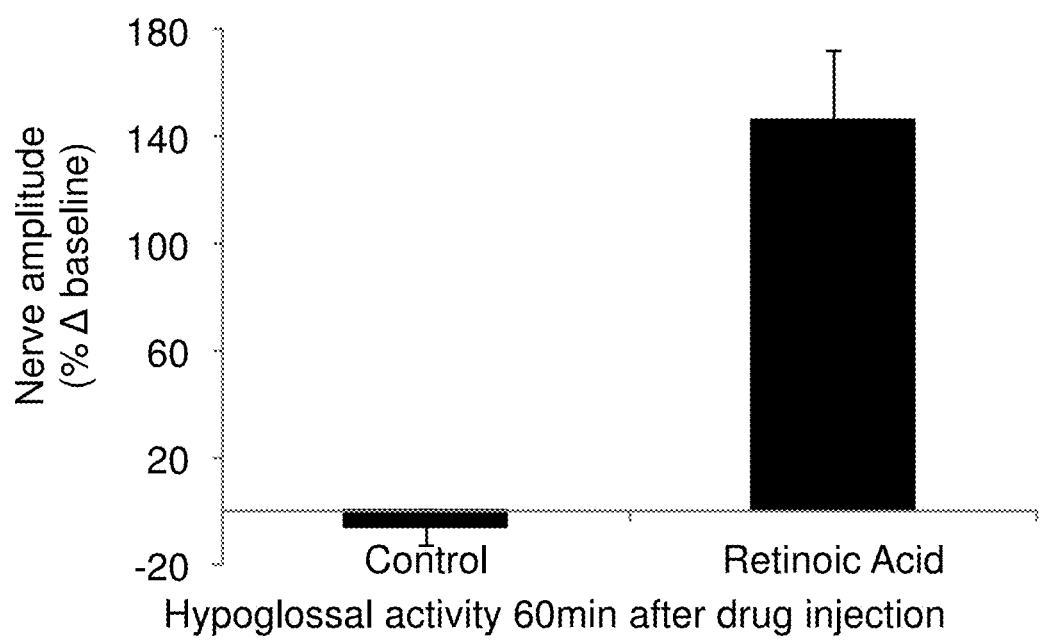
FIG. 2B is a graph depicting hypoglossal nerve activity as a percentage of baseline activity in control rats versus rats injected with retinoic acid; measurements taken 60 min after final injection.
Figure 3:
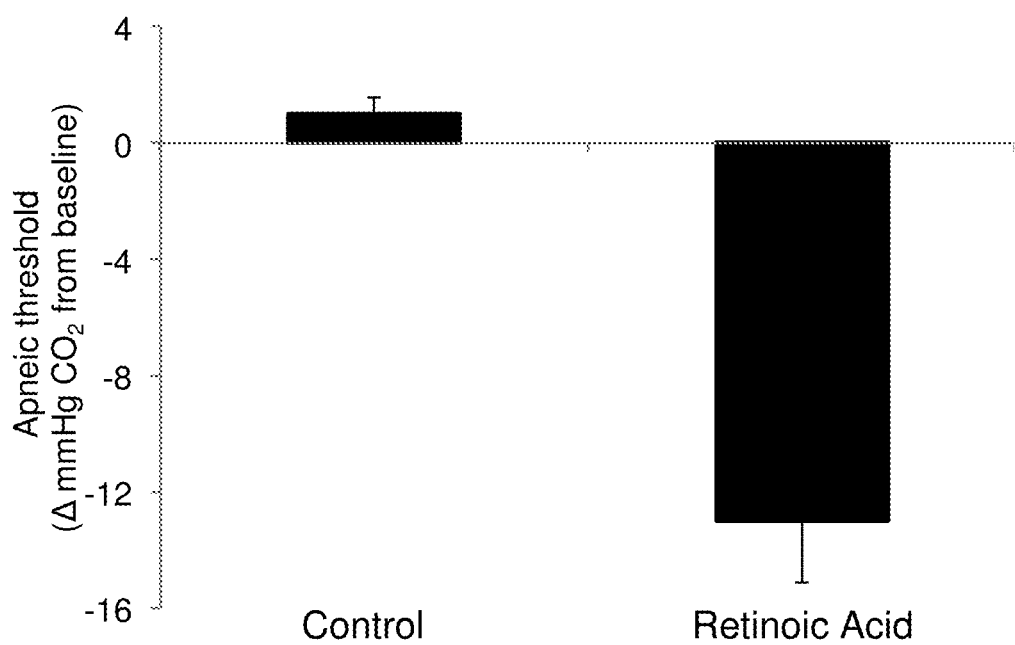
FIG. 3 is a graph depicting apneic threshold in untreated rats (control) and rats treated with all trans-retinoic acid injections. (See examples for complete details.)

Protocol 2) Five (5) brief central neural apneas followed by a 25 sec ventilator apnea (nadir $O_2$ saturation ~70%) in rats pretreated with vehicle ("control") or retinoic acid (see below for details). The results are depicted in FIGS. 2A, 2B, and 3.

Protocol 1 tests the hypothesis that retinoic acid is sufficient to elicit inactivity-induced respiratory motor facilitation. Protocol 2 tests the hypothesis that retinoic acid administration can circumvent hypoxia-induced constraints on inactivity-induced respiratory motor facilitation. Phrenic burst amplitude was recorded for up to 60 min following treatment, and an apneic threshold test was performed at the end of the protocol.

Central Neural Apnea Model:

To model a central neural apnea in anesthetized rats, inflow of $CO_2$ was ceased by stopcock valve to reduce arterial $PCO_2$ below the apneic threshold. Following a 10 second period of no phrenic firing activity (signaling absent breaths) the ventilator was turned off for 25 seconds to model the hypoxia that would normally be experienced in a human. At the end of 25 seconds, the ventilator was turned back on and $PaCO_2$ was restored. This experience was repeated five times, with five minutes separating each episode.

As shown in FIGS. 1A and 1B, retinoic acid persistently increases phrenic motor output in anesthetized rats. FIG. 1A depicts neurogram traces of phrenic nerve activity from baseline to 60 min following all trans-retinoic acid (10 μL; 50 μM) injections into the cervical spinal intrathecal space. Time of injection is noted with the upward arrows in FIG. 1A.

FIG. 1B shows that phrenic nerve activity was significantly higher than control group 60 min post-administration of trans-retinoic acid. The graphs shown in FIG. 1B represents mean±1 SEM. These results demonstrate that trans-retinoic acid elicits long-lasting respiratory motor facilitation.

FIGS. 2A and 2B demonstrate that retinoic acid injections elicit persistent increases in both phrenic and hypoglossal nerve activity in anesthetized rats in a rodent model of central neural apnea. Rats that received central neural apnea with hypoxia, but no retinoic acid ("control"), showed no persistent change in phrenic (FIG. 2A) or hypoglossal (FIG. 2B) nerve amplitude 60 min following central neural apnea, demonstrating that concurrent hypoxia undermines inactivity-induced respiratory motor facilitation of the phrenic and hypoglossal nerves. In contrast, in rats pretreated with intrathecal retinoic acid (10 μL; 50 μM) prior to central neural apneas, phrenic and hypoglossal burst amplitude were significantly higher than pre-stimulation levels, suggesting that retinoic acid treatment bypasses hypoxia-induced constraint of respiratory motor facilitation. Graphs represent mean±SEM. See FIGS. 2A and 2B, right-hand entries.

FIG. 3 demonstrates that retinoic acid protects from neural apneas by reducing the $CO_2$ apneic threshold in anesthetized rats. Retinoic acid administered prior to a central neural apnea as described above for FIGS. 1A, 1B, 2A, and 2B reduced the $CO_2$ apneic threshold relative to a control groups that did not receive the drug. Data were collected 60 min post drug (or vehicle) injections. The bars in FIG. 3 represent mean±SEM. By reducing the $CO_2$ apneic threshold, the functional $CO_2$ reserve is increased stabilizing breathing as discussed above.

Figures 4A, 4B, 4C:
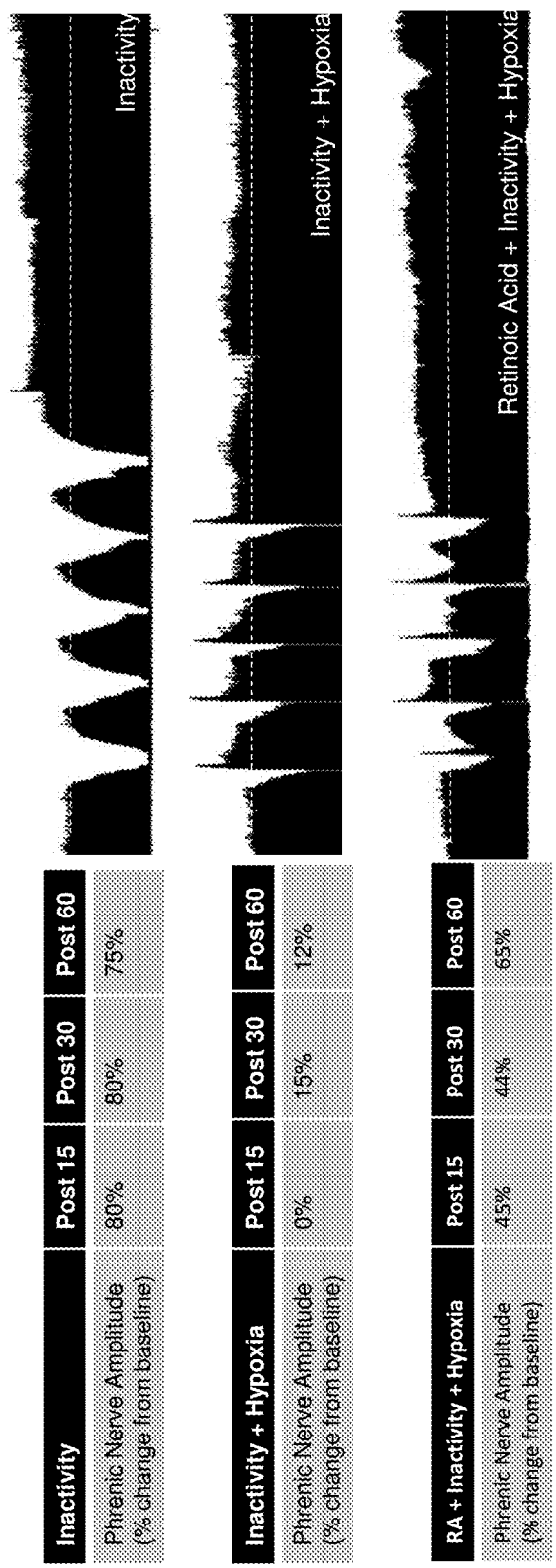
FIG. 4A is a table and corresponding recording of phrenic nerve activity showing that intermittent episodes of inactivity elicit enhanced phrenic motor output, a retinoic acid-dependent mechanism. Measurements were taken 15, 30, and 60 min after final inactivity episode.
FIG. 4B is a table and corresponding recording of phrenic nerve activity showing that intermittent inactivity with concurrent hypoxia (central sleep apnea model) abolishes the inactivity enhanced phrenic motor activity shown in FIG. 4A.
FIG. 4C is a table and corresponding recording of phrenic nerve activity showing that pretreatment with retinoic acid rescues enhanced phrenic motor output following inactivity with concurrent hypoxia.

FIGS. 4A, 4B, and 4C together provide a comparison of inactivity-induced increase in phrenic nerve activity (FIG. 4A) and how that increase in phrenic nerve activity is impacted in the presence of hypoxia (FIG. 4B) and the impact abolished by the administration of retinoic acid (FIG. 4C). FIG. 4A depicts a table and a corresponding recording of phrenic nerve activity. The recording showed that intermittent episodes of inactivity elicited enhanced phrenic motor output. The enhanced phrenic motor output is a retinoic acid-dependent mechanism. Measurements were taken 15, 30, and 60 min after final inactivity episode.

FIG. 4B is a table and corresponding recording of phrenic nerve activity showing that intermittent inactivity with concurrent hypoxia (a model of central sleep apnea abolishes the inactivity enhanced phrenic motor activity shown in FIG. 4A.

FIG. 4C is a table and corresponding recording of phrenic nerve activity showing that pretreatment of the test subjects with retinoic acid rescues then enhanced phrenic motor output following inactivity with concurrent hypoxia.

Chronic Intermittent Hypoxia:

Chronic intermittent hypoxia (CIH) is a well-studied model for mimicking physiological elements of sleep apnea (i.e., intermittent hypoxia). For a complete description of the model in rats, see Sica et al. (Jul. 12, 2000) "Chronic-intermittent hypoxia: a model of sympathetic activation in the rat," *Respir Physiol* 121(2-3):173-184. The data depicted in FIG. 5 was generated using the animal model described in the Sica et al. reference. Briefly, the experimental and control animals were placed in adjoining, identical chambers that were maintained at room temperature and were large enough to allow unimpeded movement. The fraction of inspired oxygen in each chamber was regulated by microprocessor-controlled miniature solenoids attached to each chamber by high-pressure tubing. For the CIH protocol, the chamber was flushed with 100% nitrogen for 30 sec followed by 30 sec of 100% $O_2$ at a low flow rate. The time course of change in the fraction of inspired oxygen for the experimental chamber was determined using an oxygen analyzer (Sensormedics, Milan, Italy): a decline to a nadir of 6.5 to 7% oxygen, remaining at that level for 5 to 7 sec, and then gradually increasing to 21% over the next 30 sec during which oxygen flowed into the chamber. This cycle was repeated each minute over 8 daytime hours (8 to 9 am to 4 to 5 pm) for 7 days. Control rats were exposed to the same sequence of events as experimental rats, with the exception that room air was used instead of nitrogen and oxygen. In this manner, control rats experienced the same environmental cues and degree of handling as CIH rats. At the conclusion of daily exposure protocols, animals were transferred from plastic chambers to home cages where access to food and water was freely available. All animals were maintained on a 12 h:12 h light:dark cycle.

The experimental animals were administered intra peritoneal trans-retinoic acid (500 mcg/kg) daily throughout the 7 day CIH exposure with an additional dose given the morning of diaphragm electromyography (EMG) recordings (day 8; total of 8 injections) Apneic and hypoapneic events were recorded via conventional diaphragm EMG measurements. The results are shown in FIG. 5.

Figure 5:
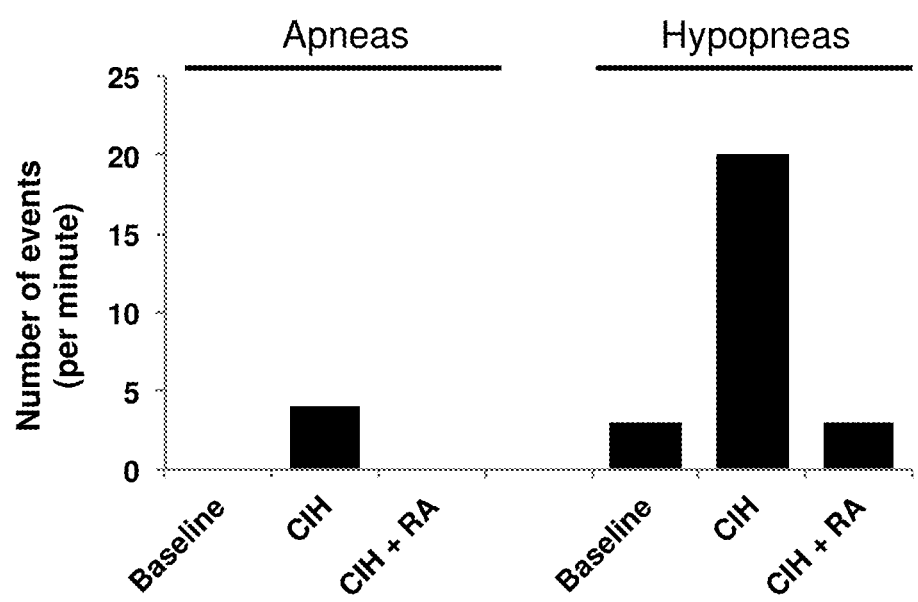
FIG. 5 is a graph depicting the efficacy of exogenous retinoic acid to inhibit the incidence of apnea and hypoapnea events in patients exhibiting chronic intermittent hypoxia (CIH). See Examples for details.

The data in FIG. 5 clearly show that CIH increases the incidence of hypopneas and apneas, which destabilize breathing activity (as measured through diaphragm EMG activity). Administering exogenous retinoic acid to the experimental animals reduces the number of apnea and hypopnea events, thus inhibiting CIH-induced breathing destabilization. This demonstrates the utility of retinoids such as RA to inhibit the onset and/or severity of central sleep apneas and obstructive sleep apneas.

What is claimed is:

1. A method of inhibiting central apnea in a mammal, the method consisting essentially of administering to a mammal a central apnea inhibitory-effective amount of a composition comprising at least one retinoid selected from the group consisting of all-trans retinoic acid, 13-cis retinoic acid, and 9-cis retinoic acid and pharmaceutically suitable salts thereof.

2. The method of claim 1, wherein the at least one retinoid is administered by inhalation.

3. The method of claim 1, wherein the at least one retinoid is administered orally.

4. The method of claim 1, wherein the at least one retinoid is administered parenterally.

5. The method of claim 1, wherein the at least one retinoid is administered enterally.

* * * * *